United States Patent [19]

Isa et al.

[11] 3,980,683

[45] Sept. 14, 1976

[54] PROCESS FOR CARBOXYLATION OF OLEFINS

[75] Inventors: Hiroshi Isa; Takeo Inagaki, both of Yachiyo; Nobuo Kojima; Isamu Kadoya, both of Tokyo, all of Japan

[73] Assignee: Lion Fat & Oil Co., Ltd., Tokyo, Japan

[22] Filed: Jan. 27, 1975

[21] Appl. No.: 544,229

[30] Foreign Application Priority Data

Feb. 9, 1974  Japan............................... 49-16663

[52] U.S. Cl.................... 260/410.9 R; 260/413; 260/497 R; 260/533 A
[51] Int. Cl.². ................. C11C 3/02; C11C 1/00; C07C 67/04
[58] Field of Search ............. 260/410.9 R, 533 A, 260/497 R, 413

[56] References Cited

UNITED STATES PATENTS

| | | | |
|---|---|---|---|
| 2,768,968 | 10/1956 | Reppe | 260/410.9 R |
| 3,507,891 | 4/1970 | Hearne | 260/410.9 R |
| 3,856,832 | 12/1974 | Ethyl | 26/410.9 R |
| 3,891,683 | 6/1975 | Isa et al. | 260/497 R |

FOREIGN PATENTS OR APPLICATIONS

| | | | |
|---|---|---|---|
| 850,675 | 9/1970 | Canada | 260/410.9 R |

*Primary Examiner*—Patrick P. Garvin
*Assistant Examiner*—John F. Niebling
*Attorney, Agent, or Firm*—Woodhams, Blanchard and Flynn

[57] ABSTRACT

A process for the carboxylation and/or alkoxycarbonylation of olefins with carbon monoxide and water or alcohol in the presence of cobalt carbonyl catalyst and also vinyl pyridine together with pyridine and/or alkyl pyridine, is disclosed.

7 Claims, No Drawings

PROCESS FOR CARBOXYLATION OF OLEFINS

BACKGROUND OF THE INVENTION

The present invention relates to a process for the carboxylation of olefins by the use of cobalt carbonyl catalyst, and particularly it relates to a process for the carboxylation of olefins which renders it possible to recover the applied cobalt carbonyl catalyst easily in reusable state.

As is generally known, when carbon monoxide together with water or carbon monoxide together with alcohol is made to react with olefins in the presence of cobalt carbonyl catalyst, there can be produced carboxylic acid or ester of carboxylic acid. On this occasion, in order to reuse the cobalt carbonyl compound applied as catalyst, it is natural that the catalyst should be recovered from the reacted mixture arising from said carboxylation reaction. As the means of recovering said catalyst, there are known two methods: one is a method of recovering the catalyst as metal cobalt through decomposition by heating the catalyst contained in the reacted mixture while blowing hydrogen or steam into said mixture, and the other is a method of recovering the catalyst in the form of cobalt salt by adding acid to the reacted mixture.

However, these conventional methods for the recovery of catalyst are all inadvisable inasmuch as they necessitate relatively complicated processes, and the metal cobalt and cobalt salt recovered thereby cannot be directly used as the carboxylation catalyst so that they must be converted into cobalt carbonyl compound for the purpose of reuse thereof.

SUMMARY OF THE INVENTION

The present invention is intended to provide a process for the carboxylation of olefins which renders it possible to recover the catalyst employed in the reaction easily and in a state in which it is suitable for reuse, and the characteristic feature thereof lies in that, at the time of effecting the carboxylation of olefins with carbon monoxide and water or alcohol in the presence of cobalt carbonyl catalyst, vinyl pyridine together with pyridine and/or alkyl pyridine is added to the reaction zone.

DESCRIPTION OF THE PREFERRED EMBODIMENTS

As the starting olefin for use in effecting the carboxylation reaction according to the present invention, $\alpha$-olefins or inner-olefins having 3–30 carbon atoms are applicable and these olefins may have side chains. To give examples of olefins of this kind, there are hexene-1, octene-2, 2-ethyl hexene-1, tetradecene-3 and their analogues. Various mixtures of these olefins are also applicable: for instance, $\alpha$-olefin mixture having 6–10 carbon atoms, $\alpha$-olefin mixture having 20–28 carbon atoms, etc. can be used as the starting olefin.

As the alcohol for use in the present invention, any aliphatic alcohol having 20 or less of carbon atoms is applicable, irrespective of whether it is a primary, secondary or tertiary alcohol or a monohydric, dihydric or polyhydric alcohol. Therefore, various kinds of alcohols illustrated by methanol, ethanol, 2-ethyl hexanol, ethylene glycol, glycerin, pentaerythritol, etc. are usable in the present invention.

The blending ratio of olefin to alcohol (or water) can be selected at will; generally speaking, however, it is desirable to be in the range of $0.01n - 10n$ moles ($n$ herein represents the number of hydroxyl group in the applied alcohol; in the case water is applied, $n=1$) of olefin per 1 mole of alcohol (or water).

Carbon monoxide for use in the present invention may contain a modicum of hydrogen as impurity, but with an increase of the content of hydrogen in said carbon monoxide, the content of impurities in the carboxylation reaction product will increase, and therefore, the lower the content of hydrogen in carbon monoxide, the better it is. The pressure for the reaction is usually set to be more than 5 $Kg/cm^2$, preferably more than 10 $Kg/cm^2$, but an elevation of pressure in excess of 300 $Kg/cm^2$ will be without value.

As the catalyst for use in the present invention, various cobalt carbonyl compounds represented by dicobalt octacarbonyl, hydrocobalt carbonyl, etc. are applicable like in the case of the conventional processes. The applicable amount of such compounds is usually in the range of 0.059–59 g in terms of cobalt metal per 1 mole of the starting olefin. In this connection, said cobalt carbonyl compounds employed as the catalyst in the present invention can be easily prepared by effecting reaction between, for instance, cobalt octylate, cobalt carbonate, cobalt oxide, etc. and carbon monoxide; on the occasion of said reaction, the coexistence of pyridine and/or alkyl pyridine as proposed in the present invention is effective for expediting the carbonylation reaction with cobalt, and it will be effective, for controlling the amount of by-product impurities coming from the carboxylation reaction of olefins to subject the resulting cobalt carbonyl to pre-treatment with vinyl pyridine in the atmosphere of elevated pressure of carbon monoxide in advance. The appropriate pressure of carbon monoxide to be applied at the time of this pre-treatment is more than 1 $Kg/cm^2$, preferably more than 10 $Kg/cm^2$. As to the temperature for said pre-treatment, any temperature will do as long as it is less than 200°C, provided that it is necessary to elevate the pressure of carbon monoxide in the case of applying a high temperature.

As discussed above, the present invention is characterized by making vinyl pyridine coexist with pyridine and/or alkyl pyridine in the reaction zone at the time of carboxylating olefins. The vinyl pyridine for this purpose means pyridine derivatives having one or more vinyl groups in the molecule thereof; to be concrete, it includes 2-vinyl pyridine, 3-vinyl pyridine, 4-vinyl pyridine, 3-methyl-4-vinyl pyridine and their analogues. The appropriate amount of these pyridines to be applied relative to the aforesaid catalyst is in the range of 0.5–10 moles, preferably 1–3 moles, per gram atom of cobalt metal contained in the catalyst.

The alkyl pyridine for use in the present invention means pyridine derivatives having 1–3 alkyl groups in the positions except for $\alpha$-position of pyridine ring, and it includes, for instance, $\beta$-picoline, $\gamma$-picoline, 4-ethyl pyridine, 3,5-lutidine. The appropriate amount of pyridine and/or alkyl pyridine relative to the aforesaid catalyst is in the range of 0.5–30 moles, preferably 1–10 moles, per gram atom of cobalt metal contained in the catalyst.

When the carboxylation of olefins is effected through the process of the present invention, the catalyst can be recovered be easily separating same from the resulting reacted mixture. In this connection, in the case where the carboxylation is effected by employing a stoichiometric excess of olefin relative to alcohol (or water), the catalyst can be easily separated to form the lower layer by merely settling the reacted mixture, while in the case where the amount of olefin employed is relatively small and the separation effect is unsatisfactory, it is possible to separate the catalyst forming the lower layer by adding an aliphatic hydrocarbon (paraffin or olefin) to the reacted mixture; in either case, the catalyst can be easily recovered. The thus recovered catalyst retains catalytic activity sufficient for use in the next carboxylation reaction as it is, and therefore, according to the process under the present invention, even when the catalyst is used repeatedly, the yield of the intended product carboxylic acid or ester of carboxylic acid is never impaired.

The mechanism of reaction between vinyl pyridine and pyridine and/or alkyl pyridine in the carboxylation reaction of olefins is yet to be clarified, but it is a recognized fact that, in the case where vinyl pyridine is independently applied, the activity of the recovered catalyst deteriorates with every recovery thereof so that the repeated use of the recovered catalyst will badly impair the yield from reaction, while in the case where pyridine and/or alkyl pyridine are applied but vinyl pyridine is not applied, it becomes difficult to recover the catalyst. Therefore, it is considered that an excellent effect such as described above can be expected only when vinyl pyridine is used together with pyridine and/or alkyl pyridine.

Hereunder will be given further elucidation of the process under the present invention by reference to a comparative example and some embodiments of the present invention. However, this does not limit the scope of the present invention.

COMPARATIVE EXAMPLE 1

0.06 Mole of cobalt oxide and 0.11 mole of γ-picoline were put in a 300 ml stainless steel autoclave and 3 hours' reaction was effected under the conditions of the hydrogen pressure being 20 Kg/cm$^2$ and carbon the monoxide pressure being 20 Kg/cm$^2$ at 160°C while stirring. After cooling, hydrogen and carbon monoxide were removed, and then 0.1 mole of decene-1 and 0.125 mole of methanol were added and 4 hours' reaction was effected under the carbon monoxide pressure of 20 Kg/cm$^2$ at 110°C while stirring. As a result, the yield of methyl undecanoate was 62%. By subjecting the reacted mixture to distillation after adding 0.12 mole of undecanoic acid thereto, there was obtained cobalt undecanoate as the distillation residue.

When the thus obtained cobalt undecanoate was put in a 300 ml stainless steel autoclave, 0.1 mole of decene-1 and 0.11 mole of γ-picoline were added thereto, and reaction was effected in the same way as above, the yield of methyl undecanoate was 27%.

EXAMPLE 1

0.06 Mole of cobalt oxide and 0.11 mole of γ-picoline were put in a 300 ml stainless steel autoclave and 3 hours' reaction was effected under the conditions of the hydrogen pressure being 20 Kg/cm$^2$ and the carbon monoxide pressure being 20 Kg/cm$^2$ at 160°C while stirring.

After cooling, hydrogen and carbon monoxide were removed, and then 0.1 mole of decene-1, 0.125 mole of methanol and 0.1 mole of 4-vinyl pyridine were added and 4 hours' reaction was effected under the carbon monoxide pressure of 20 Kg/cm$^2$ at 110°C while stirring. As a result, the yield of methyl undecanoate was 68%. And, in the lower layer of the reacted mixture, there was contained the separated catalyst. When the catalyst recovered from said reacted mixture was put in a 300 ml stainless steel autoclave, 0.1 mole of decene-1, 0.005 mole of γ-picoline and 0.125 mole of methanol were added thereto and reaction was repeatedly effected 10 times in the same way as above, the yield of methyl undecanoate was 64%.

EXAMPLE 2

0.1 Mole of cobalt oxide and 0.6 mole of 3,5-lutidine were put in a 300 ml stainless steel autoclave and 1 hour's reaction was effected under the conditions of the hydrogen pressure being 75 Kg/cm$^2$ and the carbon monoxide pressure being 75 Kg/cm$^2$ at 160°C while stirring. After cooling, hydrogen and the carbon monoxide were removed, and the reacted mixture was taken out of the autoclave. When one fourth of this reacted mixture was put in the same autoclave again, 0.5 mole of hexadecene-1, 0.04 mole of 2-vinyl pyridine and 1.0 mole of water were added thereto, and 7 hours' reaction was effected under the carbon monoxide pressure of 150 Kg/cm$^2$ at 160°C, the yield of heptadecane acids was 94%. When 1.0 mole of hexadecane was added to the resulting reacted mixture, the catalyst contained therein was separated to form the lower layer.

When the catalyst recovered from the foregoing reacted mixture was put in a 300 ml stainless steel autoclave, 0.5 mole of hexadecene-1, 0.002 mole of γ-picoline and 0.5 mole of water were added thereto and reaction was repeatedly effected 10 times in the same way as above, the yield of heptadecane acid was 91%.

EXAMPLE 3

0.04 Mole of cobalt oxide and 0.16 mole of pyridine were put in a 300 ml stainless steel autoclave and 4 hours' reaction was effected under the carbon monoxide pressure of 50 Kg/cm$^2$ at 150°C while stirring. After cooling, carbon monoxide was removed, 0.8 mole of a hexene mixture, 0.1 mole of pentaerythritol and 0.05 mole of 4-vinyl pyridine were added and 4 hours' reaction was effected under the carbon monoxide pressure of 50 Kg/cm$^2$ at 140°C while stirring. After cooling, carbon monoxide was removed, and the reacted mixture was taken out of the autoclave. This reacted mixture was in two layers. Analysis conducted after removing the unreacted olefin from the upper layer showed that the content of tetraester in the whole ester was 99.3%.

The lower layer separated as above and the removed olefin were put in a 300 ml stainless steel autoclave, 0.4 mole of a hexene mixture and 0.1 mole of pentaerythritol were added thereto, and reaction was repeatedly effected in the same way as above. Analysis conducted after removing the unreacted olefin from the upper layer resulting from the 10th reaction showed that the content of tetraester in the whole ester was 96.4%.

What is claimed is:

1. In a process for preparing carboxylic acids, or esters thereof, which comprises the steps of reacting an olefin or a mixture of olefins having from 3 to 30 carbon atoms and either water or an alcohol having up to 20 carbon atoms, wherein the molar ratio of olefin/water or alcohol is in the range of from 0.1$n$ to 10$n$/1 and wherein $n$ is the number of the hydroxyl groups in said water or alcohol, under a carbon monoxide pressure of at least 5 kg/cm$^2$, in the presence of a cobalt carbonyl catalyst, the improvement which comprises: the reaction is carried out in the presence of (a) from 0.5 to 30 moles, per gram atom of cobalt contained in the catalyst calculated as the metal, of pyridine or an alkyl-substituted pyridine or mixture thereof, wherein said alkyl-substituted pyridine has from one to 3 alkyl groups having not more than 3 carbon atoms with the proviso that there is no alkyl group in the α-position, and in the presence of (b) from 0.5 to 10 moles, per gram atom of cobalt contained in the catalyst calculated as the metal, of vinyl-substituted pyridine.

2. A process according to claim 1, wherein said vinyl-substituted pyridine is selected from the group consisting of 2-vinyl pyridine, 3-vinyl pyridine, 4-vinyl pyridine and 3-methyl-4-vinyl pyridine, and said alkyl-substituted pyridine is selected from the group consisting of β-picoline, γ-picoline, 4-ethyl pyridine and 3,5-lutidine.

3. A process as claimed in claim 2, wherein the amount of said vinyl-substituted pyridine is from 1 to 3 moles per gram atom of cobalt contained in said catalyst calculated as the metal, and the total amount of said pyridine, or alkyl-substituted pyridine, or mixture thereof is from 1 to 10 mols, per gram atom of cobalt contained in the catalyst calculated as the metal.

4. A process as claimed in claim 1, in which said catalyst is prepared by reacting a cobalt compound selected from the group consisting of cobalt octylate, cobalt carbonate and cobalt oxide, with carbon monoxide, in the presence of said pyridine or alkyl-substituted pyridine or mixture thereof, to form a cobalt carbonyl catalyst mixed with said pyridine, or alkyl-substituted pyridine or mixture thereof, and then adding said olefin, water or alcohol and vinyl-substituted pyridine to the catalyst mixture and then effecting the reaction to prepare the carboxylic acid or ester.

5. A process as claimed in claim 1, in which the reaction is carried out with a stoichiometric excess of said olefin and after completing the reaction, the reaction mixture is allowed to settle to form a lower layer containing the catalyst, recovering said catalyst and directly utilizing same as the catalyst in another like reaction.

6. A process as claimed in claim 1, in which the reaction is carried out with a small amount of olefin and after completing the reaction, a paraffin or olefin is added to the reaction mixture which is then allowed to settle to form a lower layer containing the catalyst, recovering the catalyst and directly utilizing same as the catalyst in another like reaction.

7. A process for preparing carboxylic acids, or esters thereof, which comprises the steps of:

reacting a cobalt compound with carbon monoxide in the presence of from 0.5 to 30 moles, per gram atom of cobalt calculated as the metal, of pyridine or alkyl-substituted pyridine or mixture thereof, wherein said alkyl-substituted pyridine has from 1 to 3 alkyl groups having not more than 3 carbon atoms with the proviso that said alkyl group or groups is not at the α-position, and obtaining a catalyst composition consisting of cobalt carbonyl and said pyridine or alkyl-substituted pyridine, or mixture thereof;

forming a reaction mixture consisting essentially of said catalyst composition, an olefin or mixture of olefins having from 3 to 30 carbon atoms, either water or an alcohol having up to 20 carbon atoms and a vinyl pyridine compound, in which the molar ratio of olefin/water or alcohol is from $0.01n$ to $10n/1$ wherein $n$ is the number of hydroxyl groups of said water or alcohol, the amount of cobalt calculated as the metal is from 0.059 to 59 g per one mole of said olefin, and the amount of said vinyl pyridine compound is from 0.5 to 10 moles per gram atom of cobalt calculated as the metal, and maintaining said reaction mixture under a carbon monoxide pressure of more than 5 Kg/cm$^2$ at a reaction temperature effective to transform said olefin to an acid when water is used or to an ester when an alcohol is used, separating the catalyst from the reaction mixture, and recovering said acid or ester from the reaction mixture.

* * * * *